US011491003B2

(12) United States Patent
Arbefeuille et al.

(10) Patent No.: US 11,491,003 B2
(45) Date of Patent: Nov. 8, 2022

(54) CONSTRAINABLE STENT GRAFT, DELIVERY SYSTEM AND METHODS OF USE

(71) Applicant: Bolton Medical, Inc., Sunrise, FL (US)

(72) Inventors: Samuel Arbefeuille, Sunrise, FL (US); Nico Bahar, Sunrise, FL (US)

(73) Assignee: Bolton Medical, Inc., Sunrise, FL (US)

( * ) Notice: Subject to any disclaimer, the term of this patent is extended or adjusted under 35 U.S.C. 154(b) by 39 days.

(21) Appl. No.: 16/414,292

(22) Filed: May 16, 2019

(65) Prior Publication Data

US 2019/0269498 A1  Sep. 5, 2019

Related U.S. Application Data

(63) Continuation of application No. PCT/US2018/019342, filed on Feb. 23, 2018.
(Continued)

(51) Int. Cl.
*A61F 2/07* (2013.01)
*A61F 2/89* (2013.01)
(Continued)

(52) U.S. Cl.
CPC ............ *A61F 2/07* (2013.01); *A61F 2/89* (2013.01); *A61F 2/90* (2013.01); *A61F 2/95* (2013.01);
(Continued)

(58) Field of Classification Search
CPC .... A61F 2/07; A61F 2/89; A61F 2/915; A61F 2002/075; A61F 2/90; A61F 2/95
See application file for complete search history.

(56) References Cited

U.S. PATENT DOCUMENTS

| 5,123,917 A | 6/1992 | Lee |
| 5,507,769 A | 4/1996 | Marin et al. |

(Continued)

FOREIGN PATENT DOCUMENTS

| CN | 105832447 A | 8/2016 |
| EP | 1847234 A1 | 10/2007 |

(Continued)

OTHER PUBLICATIONS

International Preliminary Report on Patentability for International Application No. PCT/US2018/019342 dated Aug. 27, 2019.
(Continued)

*Primary Examiner* — Christopher D. Prone
(74) *Attorney, Agent, or Firm* — Foley Hoag LLP (57) ABSTRACT

A stent graft for treating an arterial aneurysm includes a ligature traversing at least a portion of struts of stents, the ligature having ends that, when linked, at least partially constrict a radial dimension of the stents. The ends of the ligature can be linked by a wire in a stent graft delivery system that threads anchor loops longitudinally spanning ends of the ligature to maintain the stent in a radially constricted position during delivery to the aneurysm. The stent graft can be implanted at the aneurysm by retracting the wire from the linked ends of the ligature and from the anchor loops, thereby releasing the associated stent from the radially constricted position.

9 Claims, 10 Drawing Sheets

Related U.S. Application Data (60) Provisional application No. 62/463,057, filed on Feb. 24, 2017.

(51) Int. Cl.
| | |
|---|---|
| *A61F 2/90* | (2013.01) |
| *A61F 2/95* | (2013.01) |
| *A61F 2/962* | (2013.01) |
| *A61F 2/82* | (2013.01) |
| *A61F 2/06* | (2013.01) |
| *A61F 2/966* | (2013.01) |

(52) U.S. Cl.
CPC ........ *A61F 2/962* (2013.01); *A61F 2002/061* (2013.01); *A61F 2002/075* (2013.01); *A61F 2002/825* (2013.01); *A61F 2002/9511* (2013.01); *A61F 2002/9665* (2013.01); *A61F 2220/0016* (2013.01); *A61F 2250/0039* (2013.01)

(56) References Cited

U.S. PATENT DOCUMENTS

| | | |
|---|---|---|
| 5,755,769 A | 5/1998 | Richard et al. |
| 5,873,906 A * | 2/1999 | Lau .................. A61F 2/844 128/898 |
| 6,113,623 A | 9/2000 | Sgro |
| 6,171,334 B1 | 1/2001 | Cox |
| 6,280,464 B1 | 8/2001 | Hayashi |
| 6,395,018 B1 | 5/2002 | Castaneda |
| 7,435,253 B1 | 10/2008 | Hartley et al. |
| 7,637,940 B2 | 12/2009 | Kocur et al. |
| 7,763,063 B2 | 7/2010 | Arbefeuille et al. |
| 8,007,605 B2 | 8/2011 | Arbefeuille et al. |
| 8,062,345 B2 | 11/2011 | Ouellette et al. |
| 8,172,895 B2 | 5/2012 | Anderson et al. |
| 8,236,040 B2 | 8/2012 | Mayberry et al. |
| 8,480,725 B2 | 7/2013 | Rasmussen et al. |
| 8,486,129 B2 | 7/2013 | Lautherjung |
| 8,500,792 B2 | 8/2013 | Berra |
| 8,641,752 B1 | 2/2014 | Holm et al. |
| 8,808,351 B2 | 8/2014 | Osborne |
| 8,926,693 B2 | 1/2015 | Duffy et al. |
| 9,101,455 B2 | 8/2015 | Roeder et al. |
| 9,101,506 B2 | 8/2015 | Arbefeuille et al. |
| 9,259,336 B2 | 2/2016 | Schaeffer et al. |
| 9,364,314 B2 | 6/2016 | Berra et al. |
| 9,375,308 B2 | 6/2016 | Norris |
| 9,439,751 B2 | 9/2016 | White et al. |
| 9,592,112 B2 | 3/2017 | Arbefeuille et al. |
| 9,827,123 B2 | 11/2017 | Arbefeuille et al. |
| 9,861,503 B2 | 1/2018 | Barthold et al. |
| 9,877,857 B2 | 1/2018 | Arbefeuille et al. |
| 10,005,269 B2 | 6/2018 | Hall et al. |
| 10,080,674 B2 | 9/2018 | Yuan et al. |
| 10,299,951 B2 | 5/2019 | Arbefeuille et al. |
| 10,390,930 B2 | 8/2019 | Arbefeuille et al. |
| 10,617,542 B2 | 4/2020 | Chakfe et al. |
| 10,675,850 B2 | 6/2020 | Hall et al. |
| 10,898,357 B2 | 1/2021 | Arbefeuille et al. |
| 11,219,540 B2 | 1/2022 | Arbefeuille |
| 11,291,572 B2 | 4/2022 | Garcia |
| 2002/0062133 A1 | 5/2002 | Gilson et al. |
| 2002/0177890 A1 * | 11/2002 | Lenker .................. A61F 2/90 623/1.12 |
| 2002/0188344 A1 | 12/2002 | Bolea et al. |
| 2002/0193872 A1 | 12/2002 | Trout et al. |
| 2004/0073289 A1 | 4/2004 | Hartley |
| 2005/0119722 A1 | 6/2005 | Styrc et al. |
| 2005/0131517 A1 | 6/2005 | Hartley et al. |
| 2005/0131518 A1 | 6/2005 | Hartley et al. |
| 2005/0131519 A1 | 6/2005 | Hartley |
| 2005/0131523 A1 | 6/2005 | Bashiri et al. |
| 2006/0015171 A1 | 1/2006 | Armstrong |
| 2006/0020319 A1 | 1/2006 | Kim et al. |
| 2006/0184226 A1 | 8/2006 | Austin |
| 2007/0055360 A1 | 3/2007 | Hanson et al. |
| 2007/0135904 A1 | 6/2007 | Eidenschink et al. |
| 2007/0213805 A1 * | 9/2007 | Schaeffer .................. A61F 2/07 623/1.13 |
| 2007/0233223 A1 | 10/2007 | Styrc |
| 2008/0091260 A1 | 4/2008 | Pomeranz et al. |
| 2008/0269867 A1 | 10/2008 | Johnson |
| 2010/0004730 A1 | 1/2010 | Benjamin et al. |
| 2010/0121429 A1 | 5/2010 | Greenan et al. |
| 2010/0234932 A1 | 9/2010 | Arbefeuille et al. |
| 2010/0316830 A1 | 12/2010 | Hartley et al. |
| 2011/0190862 A1 | 8/2011 | Bashiri et al. |
| 2011/0257720 A1 | 10/2011 | Peterson et al. |
| 2012/0221096 A1 | 8/2012 | Roeder et al. |
| 2012/0271401 A1 | 10/2012 | Bruszewski et al. |
| 2013/0116773 A1 | 5/2013 | Roeder et al. |
| 2013/0116775 A1 | 5/2013 | Roeder et al. |
| 2013/0123900 A1 | 5/2013 | Eblacas et al. |
| 2013/0158648 A1 | 6/2013 | Hartley et al. |
| 2013/0184806 A1 | 7/2013 | Arbefeuille et al. |
| 2013/0245742 A1 | 9/2013 | Norris |
| 2013/0282102 A1 | 10/2013 | Peterson |
| 2013/0289713 A1 | 10/2013 | Pearson et al. |
| 2014/0039597 A9 | 2/2014 | Arbefeuille et al. |
| 2014/0046428 A1 | 2/2014 | Cragg et al. |
| 2014/0324150 A1 | 10/2014 | Stephens et al. |
| 2015/0105819 A1 | 4/2015 | Becking et al. |
| 2015/0105849 A1 | 4/2015 | Cohen et al. |
| 2015/0202065 A1 | 7/2015 | Shalev et al. |
| 2015/0202067 A1 | 7/2015 | Barrand et al. |
| 2015/0272755 A1 | 10/2015 | Arbefeuille et al. |
| 2015/0335452 A1 | 11/2015 | Rao et al. |
| 2016/0184078 A1 | 6/2016 | Choubey et al. |
| 2016/0199207 A1 | 7/2016 | Treacy et al. |
| 2016/0302950 A1 | 10/2016 | Marmur et al. |
| 2017/0135807 A1 | 5/2017 | Arbefeuille et al. |
| 2017/0281382 A1 | 10/2017 | Lostetter et al. |
| 2018/0071123 A1 | 3/2018 | Arbefeuille et al. |
| 2018/0296374 A1 | 10/2018 | Chakfe et al. |
| 2019/0231571 A1 | 8/2019 | Lostetter |
| 2019/0247178 A1 | 8/2019 | Arbefeuille |
| 2019/0247179 A1 | 8/2019 | Lostetter |
| 2019/0247213 A1 | 8/2019 | Lostetter |
| 2019/0269497 A1 | 9/2019 | Arbefeuille |
| 2019/0269498 A1 | 9/2019 | Arbefeuille et al. |
| 2019/0282355 A1 | 9/2019 | Lostetter |
| 2019/0350694 A1 | 11/2019 | Arbefeuille et al. |
| 2021/0100669 A1 | 4/2021 | Arbefeuille et al. |

FOREIGN PATENT DOCUMENTS

| | | |
|---|---|---|
| EP | 1847236 A2 | 10/2007 |
| EP | 2471498 A1 | 7/2012 |
| EP | 2517672 A1 | 10/2012 |
| EP | 2735283 A1 | 5/2014 |
| EP | 2740440 A2 | 6/2014 |
| EP | 2745812 A1 | 6/2014 |
| EP | 2745813 A1 | 6/2014 |
| EP | 2749250 A1 | 7/2014 |
| EP | 2749251 A1 | 7/2014 |
| EP | 3040054 A1 | 7/2016 |
| EP | 3068339 A1 | 9/2016 |
| EP | 3078349 A1 | 10/2016 |
| EP | 3272319 A1 | 1/2018 |
| WO | WO-97/03624 A1 | 2/1997 |
| WO | WO-99/29262 A1 | 6/1999 |
| WO | WO-99/34749 A1 | 7/1999 |
| WO | WO-01/60285 A1 | 8/2001 |
| WO | WO-02/083038 A2 | 10/2002 |
| WO | WO-2005/034809 A1 | 4/2005 |
| WO | WO-2006/037086 A1 | 4/2006 |
| WO | WO-2008/130503 A2 | 10/2008 |
| WO | WO-2009/009376 A2 | 1/2009 |
| WO | WO-2009/126906 A2 | 10/2009 |
| WO | WO-2009/148594 A1 | 12/2009 |
| WO | WO-2010/024880 A1 | 3/2010 |
| WO | WO-2010/030370 A1 | 3/2010 |

(56) References Cited

FOREIGN PATENT DOCUMENTS

| WO | WO-2010/127040 A1 | 11/2010 |
| WO | WO-2012/116368 A2 | 8/2012 |
| WO | WO-2012/145823 A1 | 11/2012 |
| WO | WO-2015/070792 A1 | 5/2015 |
| WO | WO-2016/122862 A1 | 8/2016 |
| WO | WO-2017/218474 A1 | 12/2017 |
| WO | WO-2018/026768 A1 | 2/2018 |

OTHER PUBLICATIONS

International Search Report and Written Opinion for International Application No. PCT/US2018/019342 dated May 22, 2018.

* cited by examiner

CONSTRAINABLE STENT GRAFT, DELIVERY SYSTEM AND METHODS OF USE

RELATED APPLICATION

This application is a continuation of International Application No. PCT/US2018/019342, which designated the United States and was filed on Feb. 23, 2018, published in English, which claims the benefit of U.S. Provisional Application No. 62/463,057, filed Feb. 24, 2017. The entire teachings of the above applications are incorporated herein by reference.

BACKGROUND

Arterial pathologies, including aortic aneurysms, can be treated by open surgical reconstruction, or alternatively, endovascular repair, which is a minimally invasive alternative to open surgical repair. Optimizing a successful outcome of endovascular repair, however, requires assessment of the patient's anatomy and, in the case of an arterial, or, more specifically, an aortic aneurysm, an appropriate stent spanning the proximal and distal ends of the aneurysm ensures essentially complete exclusion of the aneurysm sac by anchoring of the stent graft in the aorta to minimize endoleaks. Endoleaks and post-surgical enlargement of the aneurysm site often require additional repair to seal any expansion of the aneurysm sac and, generally, must be done without significantly compromising blood flow through the surgical site to surrounding viscera and associated structures.

Therefore, a need exists for new and improved endovascular repair devices and methods to treat arterial pathologies, such as aortic aneurysms.

SUMMARY

The present invention relates to stent grafts for use in treating and repairing aortic and other arterial vascular damage, such as vascular damage associated with aortic aneurysms, including aortic aneurysms in regions of the aorta having arterial branches that supply blood to vital organs and tissues, such as thoracic aortic aneurysms, abdominal aortic aneurysms, thoracoabdominal aortic aneurysms, juxtarenal aortic aneurysms and short-neck abdominal aortic aneurysms.

In one embodiment, the invention is a stent graft that includes a luminal graft component having a proximal open end and a distal open end. A plurality of stents are distributed longitudinally along the luminal graft component, and at least one of the stents has struts that are joined to define proximal and distal apices. At least one ligature traverses at least a portion of the struts of at least one of the stents. The ligature includes ends that, when linked, at least partially radially constrict each corresponding stent. A pair of anchor loops at the luminal graft component longitudinally span the ends of each associated ligature when linked to radially constrict the corresponding stent.

In another embodiment, the invention is a stent graft delivery system that includes a stent graft. The stent graft includes a luminal graft component having a proximal open end and a distal open end, and defines a lumen. A plurality of stents are distributed longitudinally along the luminal graft component, and at least one of the stents has struts that are joined to define proximal and distal apices. At least one ligature traverses at least a portion of the struts. The ligature includes ends that, when linked, at least partially radially constrict the stent. A pair of anchor loops at the luminal graft component longitudinally span the ends of each associated ligature when linked to radially constrict the corresponding stent. A wire extends longitudinally along the luminal graft component, and through the anchor loops, linking the ligature ends and thereby radially constricting at least a portion of the stents of the stent graft, whereby retraction of the wire from the ends of the at least one ligature releases the ends of stent graft from constriction by the at least one ligature.

In still another embodiment, the invention is a method of implanting a stent graft at an arterial aneurysm of a subject. The method includes advancing a stent graft to an arterial aneurysm of the subject, wherein the stent graft includes at least one ligature extending about a periphery of the stent graft, the ligature traversing struts of a radial stent of the stent graft and having ends that are linked by a wire extending parallel to a longitudinal axis of the stent graft and through anchor loops longitudinally spanning the linked ends to thereby maintain the stent graft in a radially constricted position. The wire is retracted from the at least one ligature and the anchor loops, consequently releasing the ends of the ligature from each other, whereby the stent graft radially expands from the radially constricted position to a radially expanded position, thereby implanting the stent graft at the arterial aneurysm of the subject.

This invention has many advantages. For example, the physician can rotate or reposition the stent graft after it has been partially deployed to align a fenestration in the stent graft with a branch vessel, such as by only partially retracting the wire radially constricting stents of the stent graft, thereby providing greater control over delivery systems that are only able to position the stent graft before deployment begins. As a consequence, a stent graft can be deployed at a surgical site with more accuracy, less risk of injury to the vasculature of the subject, and without significant risk of distorting the intended shape of the stent graft when implanted at the surgical site.

BRIEF DESCRIPTION OF THE DRAWINGS

The foregoing will be apparent from the following more particular description of example embodiments, as illustrated in the accompanying drawings in which like reference characters refer to the same parts throughout the different views. The drawings are not necessarily to scale, emphasis instead being placed upon illustrating embodiments. The same number present in different figures represents the same item.

DETAILED DESCRIPTION

A description of example embodiments follows.

The invention is generally directed to a stent graft and a delivery system that includes a stent graft and a plurality of wires extending through the lumen of the stent graft and on each lateral side of a fenestration in the stent graft. The invention also is directed to a method of use of the stent graft and delivery system of the invention. The stent graft delivery system and method of its us treat aortic vascular damage, such as vascular damage associated with an aortic aneurysms, including in regions of the aorta having arterial branches that supply blood to vital organs and tissues, such as thoracic aortic aneurysms, abdominal aortic aneurysms, thoracoabdominal aortic aneurysms, including juxtarenal aortic aneurysms and short-neck abdominal aortic aneurysms.

When reference is made herein to a prosthesis, also referred to herein as "stent graft," "stent graft," or "vascular prosthesis," to be delivered, or implanted in a patient, the word "proximal" means that portion of the prosthesis or component of the prosthesis that is relatively close to the heart of the patient and "distal" means that portion of the prosthesis or component of the prosthesis that is relatively far from the heart of the patient.

When, however, reference is made to a delivery system or a component of a delivery system employed to deliver, or implant, a prosthesis, the word, "proximal," as employed herein, means closer to the clinician using the delivery system. When reference is made to a delivery system or a component of a delivery system, "distal," as that term is employed herein, means, further away from the clinician using the delivery system.

For clarity, the word "proximate" means "close to," as opposed to the meanings ascribed to "proximal" or "distal" described above with respect to either the prosthesis or a delivery system.

One embodiment of a stent graft delivery system of the invention is shown in FIG. 1A through 1F. As shown therein, stent graft delivery system 10 includes stent graft 12 of the invention. Stent graft 12 includes luminal graft component 14 having proximal open end 16, distal open end 18, and outside surface 20. Inside surface 22 defines a lumen about longitudinal axis 26. Luminal graft component 14 is fabricated of a suitable material, such as is known in the art. Examples of suitable materials include expanded polytetrafluoroethylene (ePTFE) and polyethylene terephthalate (PET), such as woven polyester.

Figure 1A:
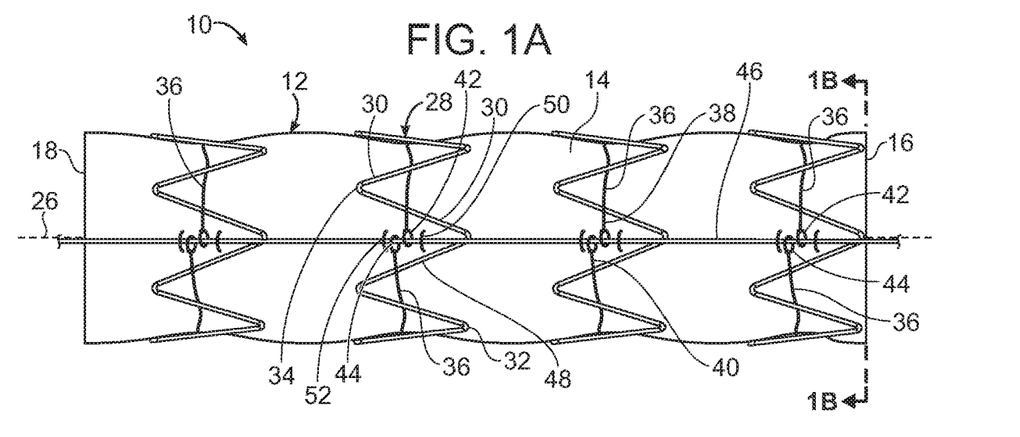
FIG. 1A is a side view of one embodiment of a stent graft delivery system of the invention, wherein a stent graft is in a radially constricted position, and a wire maintaining the stent graft in a radially constricted position is stabilized by anchor loops.

Stents 28 of stent graft 12 are distributed radially about luminal graft component 14 and longitudinally along luminal graft component 14. Stents 28 include struts 30 that are joined at either end to defined proximal apices 32 and distal apices 34. Stents 28 are fabricated of a suitable material, such as is known in the art. In one embodiment, stents 28 are fabricated of a material that causes stents to radially self-expand upon release from radial constraint. Examples of suitable materials of radial self-expanding stents include a shape memory alloy, such as Nitinol. Examples of stents not formed of a shape memory alloy include those formed of stainless steel. In embodiments of the invention that do not employ a shape memory alloy, or are otherwise not radially self-expanding, a balloon catheter, for example, can be employed to radially expand stents that have been released from radial constriction, as is known in the art. Stents 28 can also include a radiopaque component, as is known in the art, such as at least one radiopacifier selected from the group consisting of barium sulfate, bismuth, tungsten, platinum-iridium and tantalum-tungsten.

Ligatures 36 extend about luminal graft component 14 and include ends 38,40. Ligatures 36 are formed of a suitable material, such as is known in the art. Examples of suitable materials of ligatures 36 include polyester, and nylon. As shown in FIG. 1A, ends of ligatures 36 include ligature loops 42,44. Ligature loops 42,44 are linked, such as by wire 46, as shown in FIG. 1A, to constrict the diameter of stent graft 12. As represented in FIG. 1A, ligatures 36 extend between stents 28 and luminal graft material 14, and traverse struts of stents 28, where ligatures 36 extend between stents 28 and luminal graft material 14. On either immediate lateral side of wire 46, ligatures 36 traverse struts 30 by passing over a radially outwardly-facing portion 48 of struts 30. Anchor loops 50,52 are distributed longitudinally on either side of the portion of wire 46 and ligature loops 42,44 of ligatures 36 and, consequently, span ligature loops 42,44 to stabilize wire 46, at least in part, from lateral migration of wire 46 about the periphery of stent graft 12. Ligatures 36 are formed of a suitable material, such as is known in the art. Examples of suitable materials of ligatures 36 include, for example, stainless steel or a shape-memory alloy, such as Nitinol. Likewise, anchor loops 50,52 are formed of a suitable material, such as a material suitable for fabrication of ligatures 36. It is to be understood that, in certain other embodiments, anchor loops 50,52 are not present, such as in embodiments where ligatures 36 are stabilized at stent graft 12 by, for example, being threaded between luminal graft component 14 and struts 30, thereby substantially preventing lateral migration of wire 46 when wire 46 is linking end 38,40 of ligatures 36.

Returning to FIG. 1A, wire 46 extends through loops 42,44 of ligatures, thereby linking ends 38,40 of ligatures 36 and maintaining stent graft 12 in a radially constricted position. It is to be understood that, when stents 28 are formed of a shape-memory metal alloy, such as Nitinol, then ligatures 36 hold stents 28 in a radially-constricted position, wherein radially self-expanding stents 28 exert a radially outward force against ligatures 36. It is also to be understood that, in alternative embodiments, ligatures 36 can traverse struts 30 between struts 30 and luminal graft component 14, or about radially outwardly-facing portion 48 of struts 30, in different arrangements than that shown in FIG. 1A. Further, it is to be understood that ligatures 36 can pass through the fabric of luminal graft component 14 into lumen 24 in various embodiments, such as in an embodiment wherein wire 46 extends through lumen 24 and against the inside surface of luminal graft component 14, as opposed to outside surface 20 of luminal graft component 14. Also, alternatively, in certain embodiments (not shown), stents 28 can be secured to luminal graft component 14 at inside surface 22 of luminal graft component 14, in which case wire 46 would, in one possible embodiment, extend within lumen 24, and ligatures 36 would traverse struts 30 between struts 30 and the inside surface of luminal graft component 14. Other arrangements between wire 46, ligatures 36 and stents 28 are also possible.

Figure 1B:
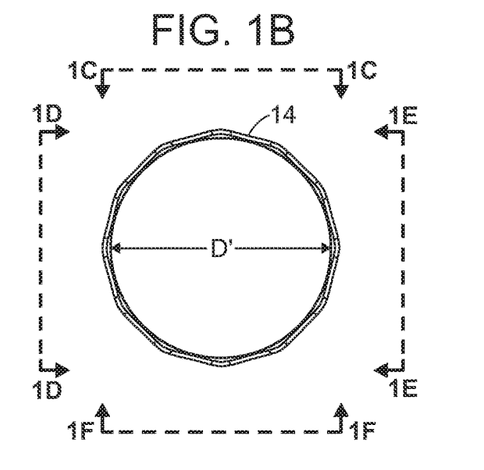
FIG. 1B is an end view of the stent graft delivery system of FIG. 1A, taken along line 1B-1B, and having diameter D'.
Figure 1C:
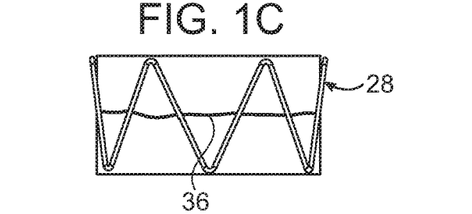
FIG. 1C is a side view of the proximal end of the stent graft of FIG. 1B taken along line 1C-1C.
Figure 1D:
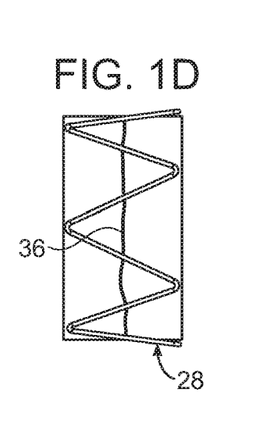
FIG. 1D is a side view of the proximal end of the stent graft of FIG. 1B taken along line 1D-1D.
Figure 1E:
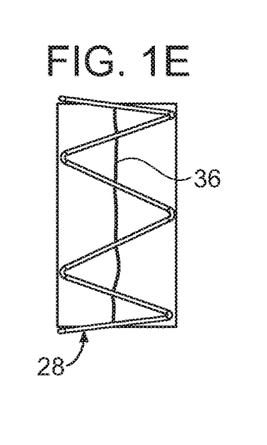
FIG. 1E is a side view of the proximal end of the stent graft of FIG. 1B taken along line 1E-1E.
Figure 1F:
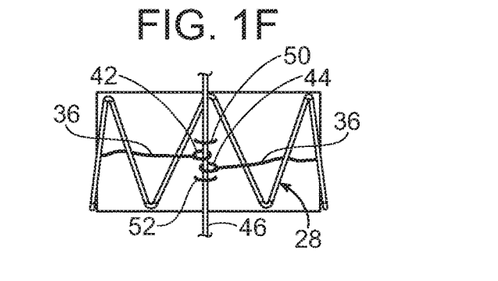
FIG. 1F is a side view of the proximal end of the stent graft of FIG. 1B taken along line 1F-1F.

FIG. 1B is an end view of stent graft 12, as shown in FIG. 1A, taken along line 1B-1B. As can be seen in FIG. 1B, constricted open stent graft 12 has an inside diameter of D'. FIG. 1C is a side view of the stent and luminal graft component at proximal open end 16 of stent graft 12 shown in FIG. 1A, as viewed from line 1C-1C of FIG. 1B. Likewise FIGS. 1D, 1E, and 1F, show side views of the most proximal stent of stent graft 12, shown in the end view of FIG. 1B, taken along lines 1D-1D, 1E-1E and 1F-1F, respectively. Collectively, FIGS. 1A-1F show ligatures 36 extending about the perimeter of stent graft 12 and between struts 30 and luminal graft component 14, except for struts 30 on either lateral side of wire 46, where ligatures 36 pass over an outwardly-facing portion 48 of struts 30.

Figure 2A:
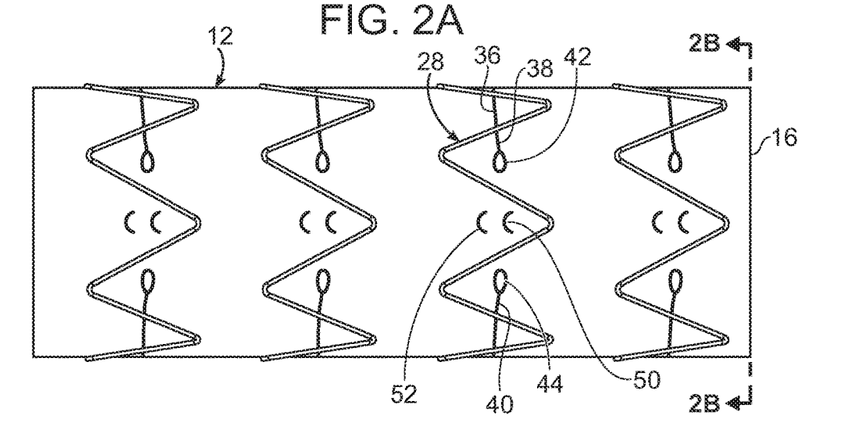
FIG. 2A is a side view of the stent graft shown in FIGS. 1A-1F, following retraction of the wire linking ligatures holding the stent graft in a radially constricted position.
Figure 2B:
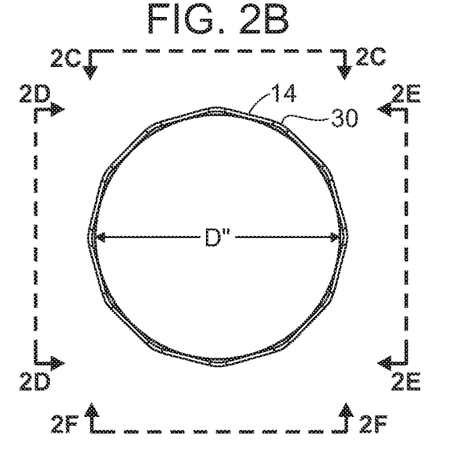
FIG. 2B is an end view of the proximal end of the stent graft in an unconstricted position, as shown in FIG. 2A, taken along line 2B-2B, and having an expanded diameter D.
Figure 2C:
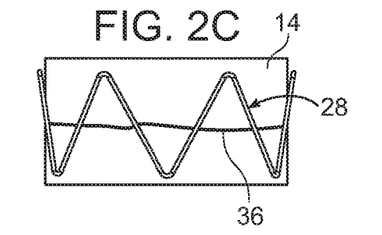
FIG. 2C is a side view of the proximal end of the stent graft shown in FIG. 2B, taken along line 2C-2C.
Figure 2D:
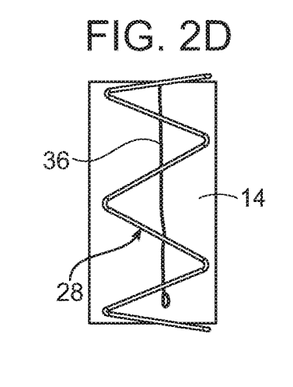
FIG. 2D is a side view of the proximal end of the stent graft shown in cross-section in 2B, taken along line 2D-2D.
Figure 2E:
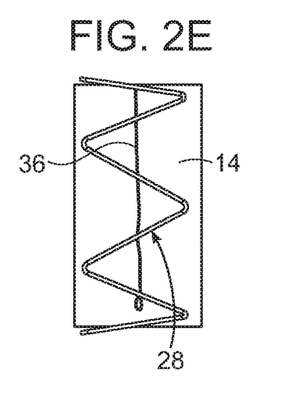
FIG. 2E is a side view of the proximal end of the stent graft shown in FIG. 2A and shown in cross-section in FIG. 2B, taken along line 2E-2E.
Figure 2F:
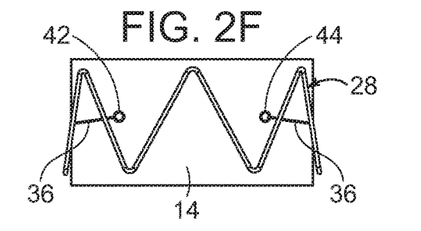
FIG. 2F is a side view of the proximal end of the stent graft shown in FIG. 2B taken along line 2F-2F.

FIG. 2A is a side view of stent graft 12 shown in FIG. 1A, but following retraction of wire 46 from anchor loops 50,52 and loops 42,44 of ligatures 36, thereby allowing radial expansion of stents 28 from the constricted position, shown in FIGS. 1A-1F, to an expanded position, shown in FIG. 2A. Radial expansion of stents 28, such as by expansion of radially self-expanding stents 28 fabricated of, for example, Nitinol, causes ends 38,40 and, specifically, loops 42,44 of ligatures 36 to separate from each other and from anchor loops 50,52 longitudinally spanning wire loops 42,44 where wire 46 had previously linked loops 42,44 between anchor loops 50,52. FIG. 2B is an end view of stent graft 12 of FIG. 2A, taken along line 2B-2B, showing an expanded internal diameter D″ following release of stent graft 12 from the radially constricted position represented in FIGS. 1A-1F. FIGS. 2C, 2D, 2E and 2F show side views of the most proximal stent and the luminal graft component at proximal open end 16 represented in FIG. 2B, taken along lines 2C-2C, 2D-2D, 2E-2E, and 2F-2F respectively.

Figure 3A:
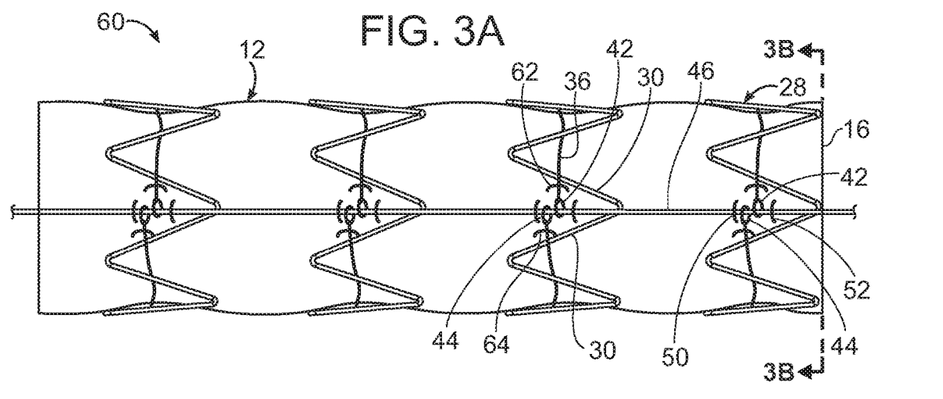
FIG. 3A is another embodiment of a stent graft delivery system of the invention, wherein a stent graft of the stent graft delivery system is held in a radially constricted position by a wire stabilized by anchor loops, and wherein the ligatures are stabilized by ligature loops distributed laterally on either side of the wire.
Figures 3B, 3E:
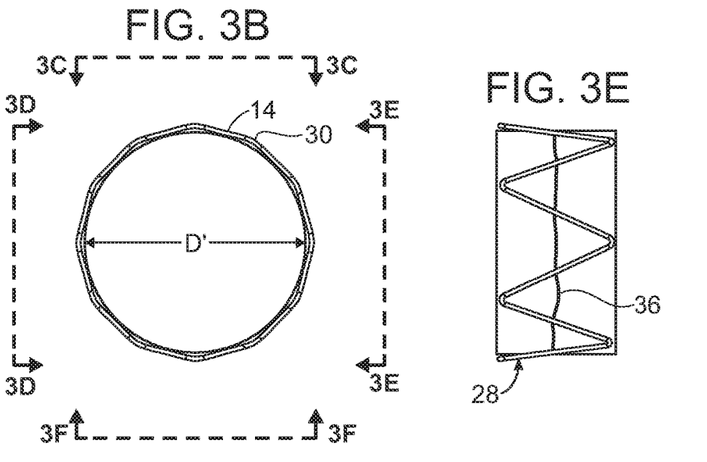
FIG. 3B is an end view of the stent graft delivery system shown in FIG. 3A, taken along line 3B-3B, showing the stent graft as having a constricted diameter D'.
FIG. 3E is a side view of the proximal end of the stent graft shown in FIG. 3B, taken along line 3E-3E.
Figure 3C:
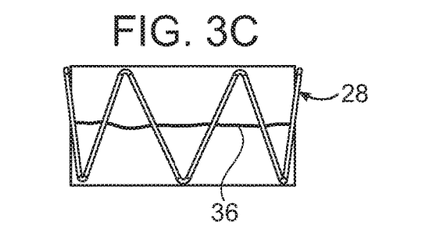
FIG. 3C is a side view of the proximal end of stent graft shown in FIG. 3B, taken along line 3C-3C.
Figure 3D:
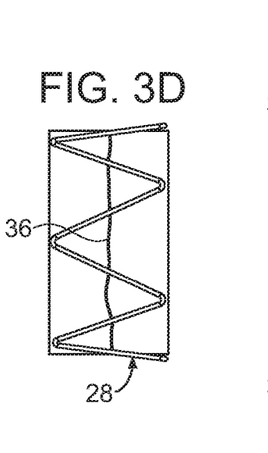
FIG. 3D is a side view of the proximal end of the stent graft shown in FIG. 3B, taken along line 3D-3D.
Figure 3F:
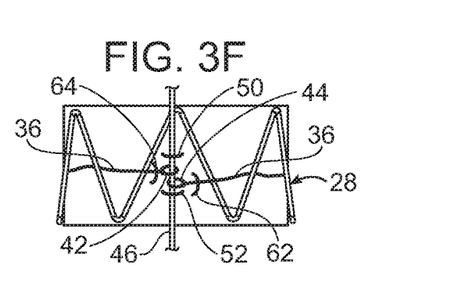
FIG. 3F is a side view of the proximal end of the stent graft shown in FIG. 3B, taken along line 3F-3F.

FIG. 3A is a side view of another embodiment of the stent graft delivery system of the invention. As shown therein, stent graft delivery system 60 additionally supports ligatures 36 by ligature sutures 62,64 at stent graft 12 between each loop 42,44 and struts 30 they traverse on either side of wire 46. The arrangement of ligature sutures 62,64 between loops 42,44 and respective struts 30 traversed by ligatures 36 stabilizes linkage of loops 42,44 by wire 46. It is to be understood that, in still another embodiment, ligature sutures 62,64 can be employed in the alternative to anchor loops 50,52 to thereby stabilize loops 42,44 when linked by wire 46. FIG. 3B is an end view of proximal open end 16 of stent graft 12 shown in FIG. 3A, taken along line 3B-3B, and showing inside diameter D′ of most radially constricted stent graft 12. FIGS. 3C, 3D, 3E and 3F, show side views of the most proximal stent 28 and luminal graft component at proximal open end 16 shown in cross-section in FIG. 3B, taken along lines 3C-3C, 3D-3D, 3E-3E, and 3F-3F, respectively.

Figure 4A:
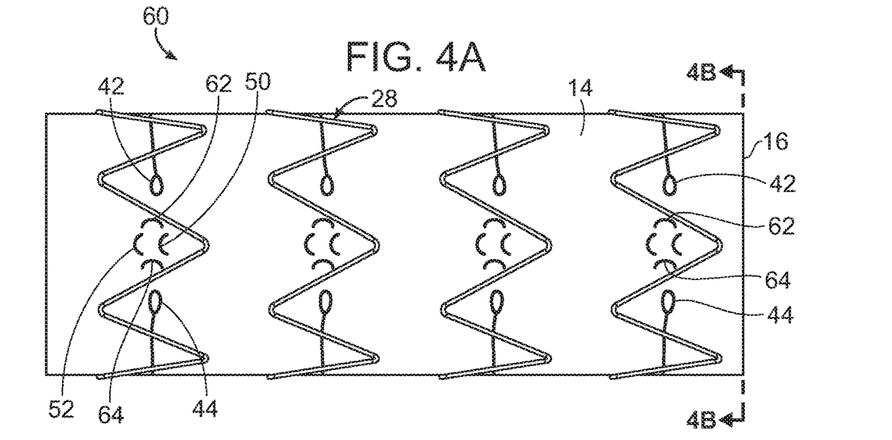
FIG. 4A is a side view of the stent graft of the stent graft delivery system shown in FIGS. 3A-3F, following retraction of the wire component of the stent graft delivery system from end loops of the ligatures and from the anchor loops, thereby causing stent graft to expand in diameter to an expanded position.
Figure 4B:
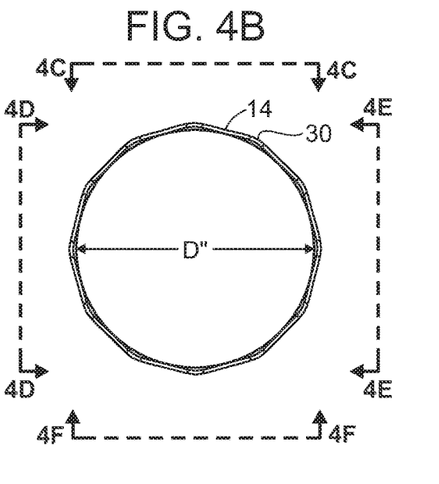
FIG. 4B is an end view of the stent graft as shown in FIG. 4A, taken along lines 4B-4B, having an expanded diameter D.
Figure 4C:
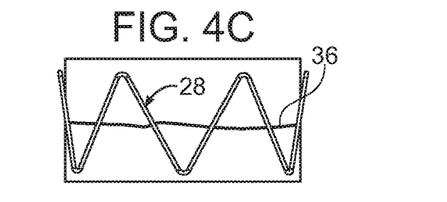
FIG. 4C is a side view of the proximal end of the stent graft shown in FIG. 4B, taken along line 4C-4C.
Figure 4D:
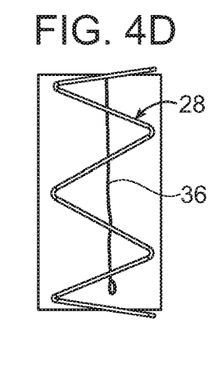
FIG. 4D is a side view of the proximal end of the stent graft shown in FIG. 4B, taken along line 4D-4D.
Figure 4E:
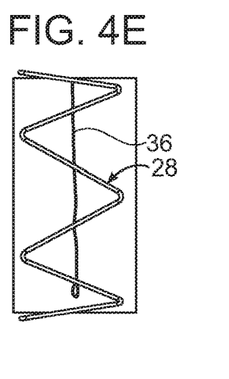
FIG. 4E is a side view of the proximal end of the stent graft shown in FIG. 4B, taken along line 4E-4E
Figure 4F:
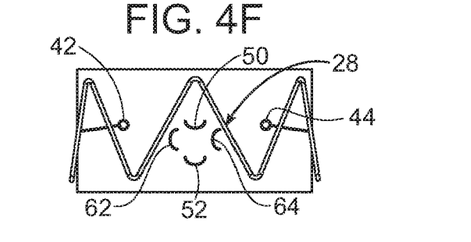
FIG. 4F is a side view of the proximal end of the stent graft shown in FIG. 4B, taken along line 4F-4F.

FIG. 4A is a side view of stent graft delivery system 60 shown in FIG. 3A, following retraction and withdrawal of wire 46 from anchor loops 50,52 and linkage of loops 42,44. As can be seen therein, radial expansion of stents 28 from a radially constricted position to a radially expanded position causes loops 42,44 to laterally separate from each other and, as shown in FIG. 4A, to retract from the ligature sutures 62,64, respectively. FIG. 4B is an end view of the stent graft in a radially expanded position, as shown in FIG. 4A, taken along line 4B-4B, showing the expanded inside diameter D″ following radial expansion of stent 28 at that section. FIGS. 4C, 4D, 4E, and 4F, show side views of the most proximal stent 28 and luminal graft component 14 at the most proximal stent 28 shown in cross-section in FIG. 4B, taken along lines 4C-4C, 4D-4D, 4E-4E, and 4F-4F, respectively.

Figure 5A:
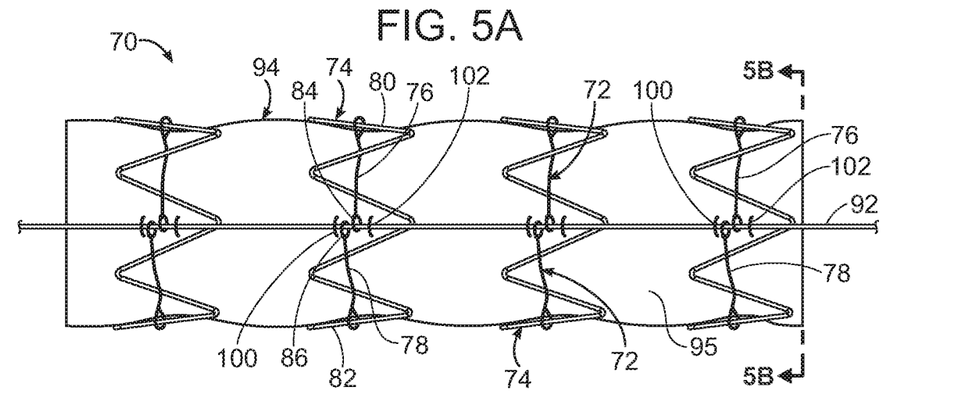
FIG. 5A is a side view of another embodiment of the stent graft delivery system of the invention, wherein ligatures do not completely encompass the stent graft when the prosthesis is in a radially constricted position.
Figure 5B:
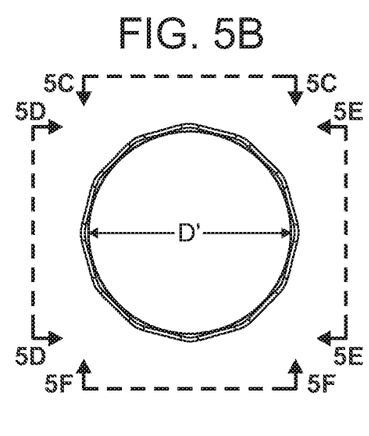
FIG. 5B is an end view of the stent graft delivery system shown in FIG. 5A, taken along line 5B-5B, showing the stent graft having a constricted diameter D'.
Figure 5C:
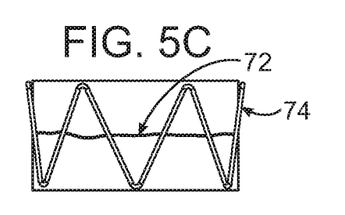
FIG. 5C is a side view of the proximal end of the stent graft shown in FIG. 5B, taken along line 5C-5C.
Figure 5D:
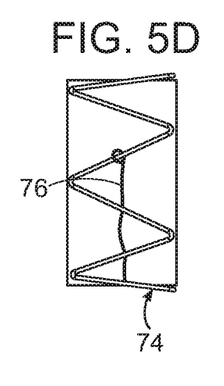
FIG. 5D is a side view of the proximal end of the stent graft shown in FIG. 5B, taken along line 5D-5D.
Figure 5E:
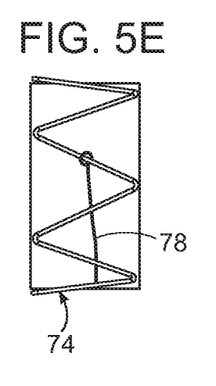
FIG. 5E is a side view of the proximal end of the stent graft shown in FIG. 5B, taken along line 5E-5E.
Figure 5F:
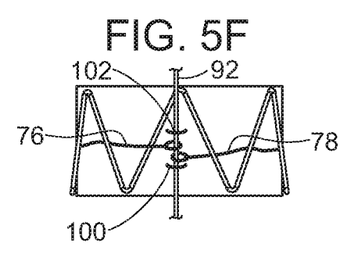
FIG. 5F is a side view of the proximal end of the stent graft shown in FIG. 9B, taken along line 5F-5F.

FIG. 5A is a side view of yet another embodiment of a stent graft delivery system of the invention. As shown in FIG. 5A, stent graft delivery system 70 includes ligatures 72 at each stent 74 of stent graft 94. Ligatures 72 include two component parts 76,78, each of which is secured at separate struts 80,82 of respective stent 74. Ligatures 72 include loops 84,86 at each end that are aligned by wire 92, which passes through them, thereby maintaining stent graft 94 in a constricted position. Ligature parts 76,78 are stabilized by anchor loops 100,102 longitudinally spanning loops 84,86 when wire 92 is threaded through loops 84,86, thereby radially constricting stents 74. Although not shown, it is to be understood, that ligature sutures can, optionally, also be employed, as described with respect to FIGS. 1A and 3A. FIG. 5B is an end view of the stent graft delivery system 70 shown in FIG. 5A, taken along line 5B-5B, showing an internal diameter D′ of stent graft 94 in a radially constricted position. FIGS. 5C, 5D, 5E, 5F, show side views of the most proximal stent 74 and the portion of the luminal graft component at the most proximal stent 74, shown in FIG. 5B taken along lines 5C-5C, 5D-5D, 5E-5E and 5F-5F, respectively.

Figure 6A:
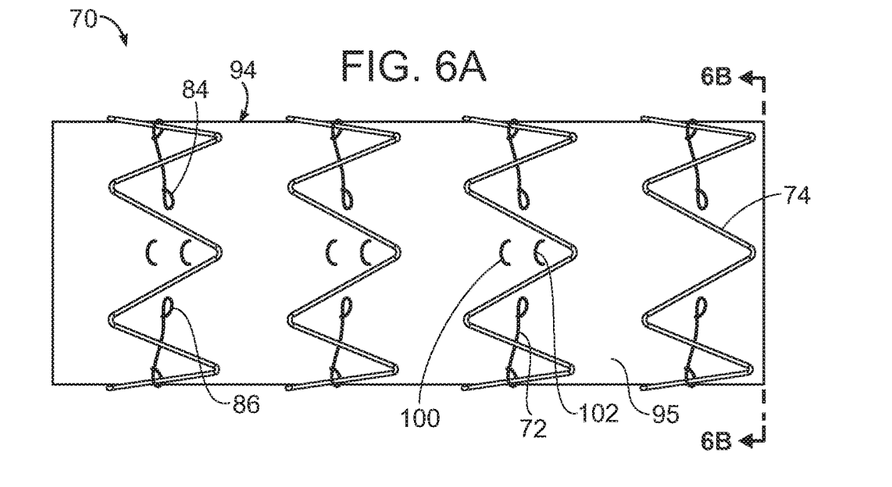
FIG. 6A is a side view of the stent graft of the stent delivery system shown in FIGS. 5A-5F, following retraction of the wire linking ends of the ligature to hold the stent graft in a radially constricted position, wherein retraction of the wire from the anchor loops causes the stent graft to radially expand to an expanded diameter.
Figure 6B:
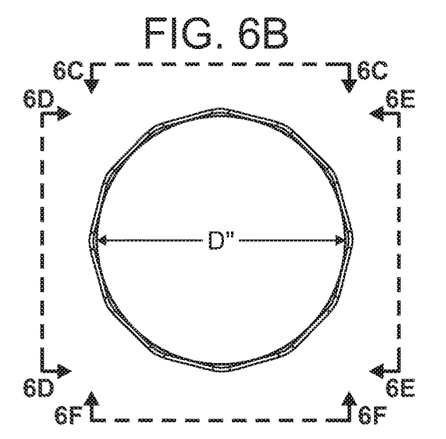
FIG. 6B is an end view of the proximal end of the stent graft shown in FIG. 6A, taken along line 6B-6B, showing the diameter of the radially expanded stent graft as D.
Figure 6C:
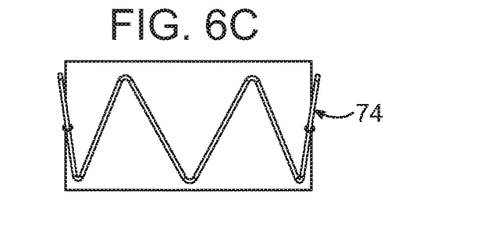
FIG. 6C is a side view of the proximal end of the stent graft shown in FIG. 6B, taken along line 6C-6C.
Figure 6D:
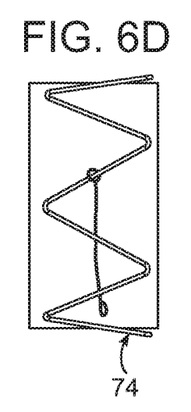
FIG. 6D is a side view of the proximal end of the stent graft shown in FIG. 6B, taken along line 6D-6D.
Figure 6E:
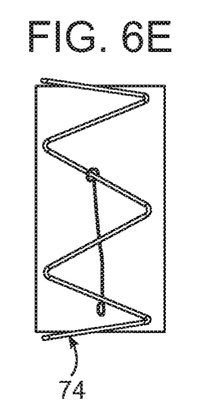
FIG. 6E is a side view of the proximal end of the stent graft shown in FIG. 6 taken along line 6E-6E.
Figure 6F:
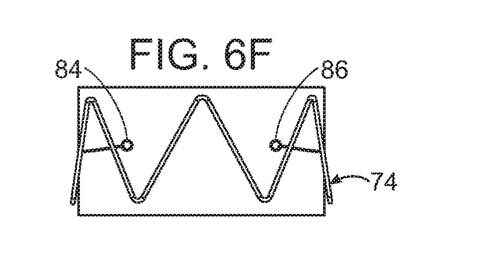
FIG. 6F is a side view of the proximal end of the stent graft shown in FIG. 6B, taken along line 6F-6F.

FIG. 6A is a side view of stent graft 94 shown in FIG. 5A, following retraction of wire 92 from anchor loops 100,102 and loops 82,84 of ligatures 72, thereby allowing stent graft 94 to radially expand from the radially constricted position, shown in FIGS. 5A-5F, to a radially expanded position, shown in FIG. 6A. As can be seen in FIG. 6A, loops 84,86 laterally separate from each other, and from anchor loops 100,102 upon radial expansion of stent graft 94 from the radially constricted state to the expanded state. FIG. 6B is an end view of stent graft 94 shown in FIG. 6B, taken along line 6B-6B, showing a radially expanded internal diameter D″ of stent graft 94. FIGS. 6C, 6D, 6E, and 6F, show side views of the most proximal stent 74 and the portion of luminal graft component 95 most proximate to the most proximal stent 74, shown in FIG. 6B, taken along lines 6C-6C, 6D-6D, 6E-6E, and 6F-6F, respectively.

Figure 7A:
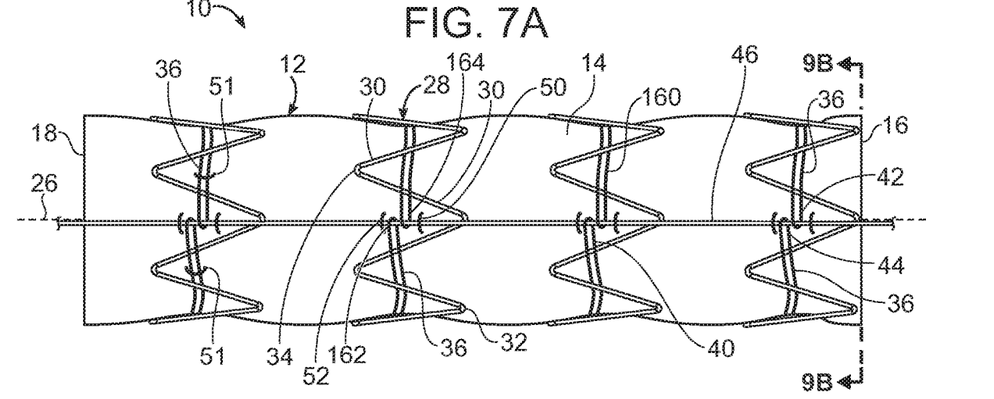
FIG. 7A is a side view of yet another embodiment of a stent graft delivery system of the invention, wherein ligatures radially constricting the stent graft are circular and extend about the periphery of the stent graft, and wherein diametrically opposed points of the ligatures are linked by a wire that is stabilized by anchor loops.
Figure 7B:
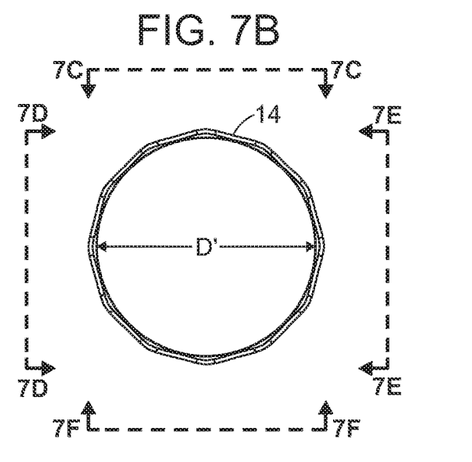
FIG. 7B is an end view of the stent graft delivery system of FIG. 7A, taken along line 7B-7B, and having diameter D'.
Figure 7C:
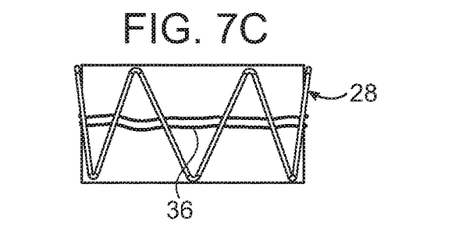
FIG. 7C is a side view of the proximal end of the stent graft shown in FIG. 7B taken along line 7C-7C.
Figure 7D:
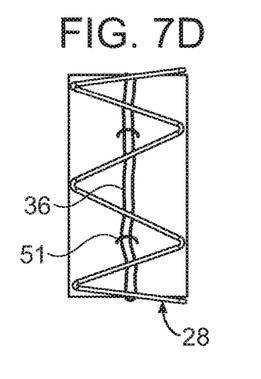
FIG. 7D is a side view of the proximal end of the stent graft shown in FIG. 7B taken along line 7D-7D.
Figure 7E:
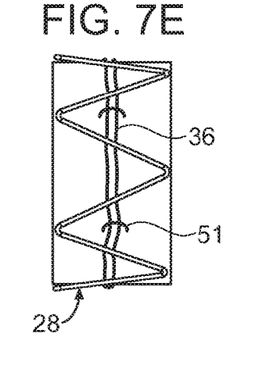
FIG. 7E is a side view of the proximal end of the stent graft shown in FIG. 7B taken along line 7E-7E.
Figure 7F:
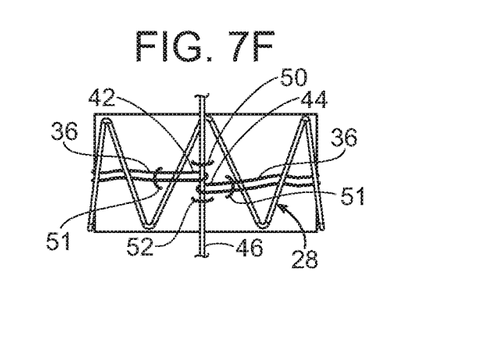
FIG. 7F is a side view of the proximal end of the stent graft shown in FIG. 7B taken along line 7F-7F.

In another embodiment, circular ligatures 160 extend about the periphery of stent graft 12 to form distally opposed ends 162,164 of circular ligatures 160 that are linked by wire 46. Wire 46 is stabilized by anchor loops 50,52 at the stent graft as shown in FIGS. 7A, 7F. Ligature sutures 51 are arranged laterally at luminal graft component 14 through which the ligature ends 162,164 pass, ligature sutures 51 being located on either lateral side of wire 46 passing through anchor loops 50,52, and wherein ligature ends 162,164 are linked by wire 46 between ligature sutures 51.

Figure 8A:
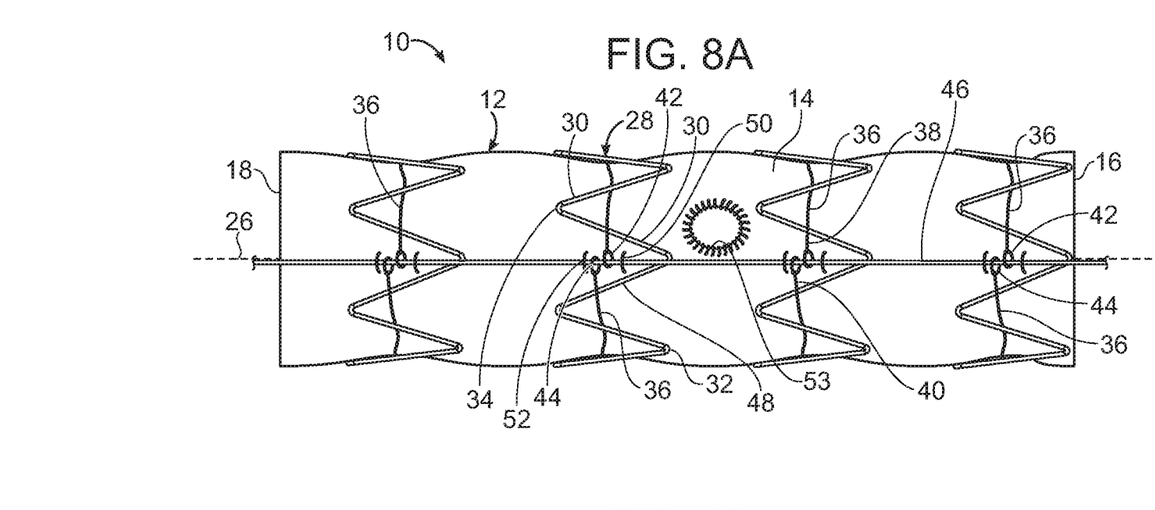
FIG. 8A is a side view of another embodiment of a stent graft delivery system of the invention, wherein the stent graft includes a fenestration.
Figure 8B:
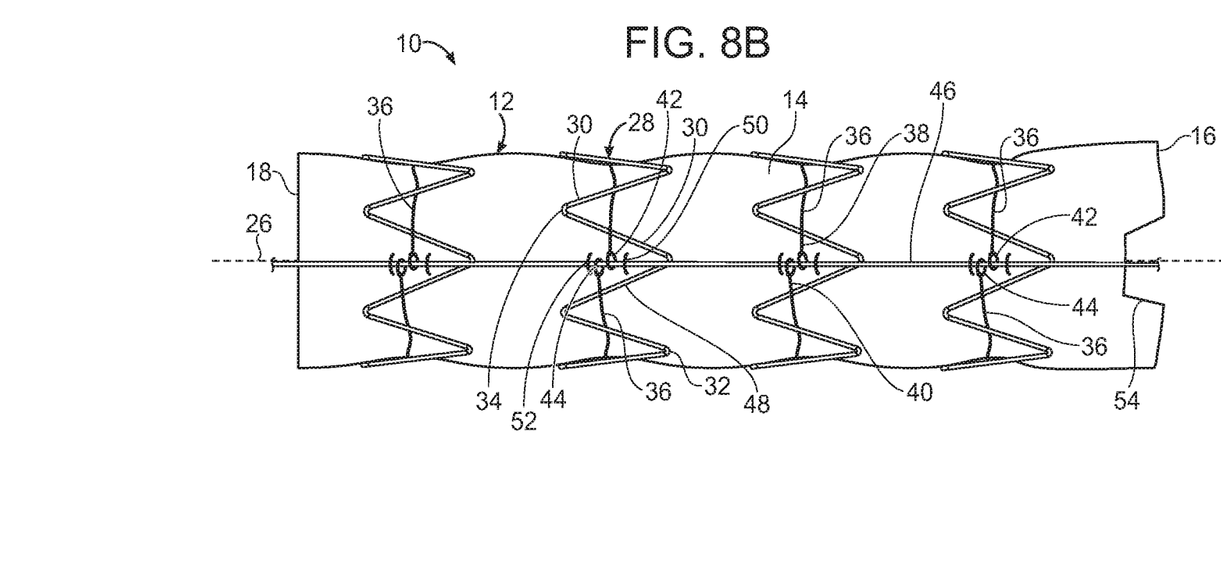
FIG. 8B is a side view of yet another embodiment of a stent graft delivery system of the invention, wherein the proximal open end includes a scalloped edge.
Figure 8C:
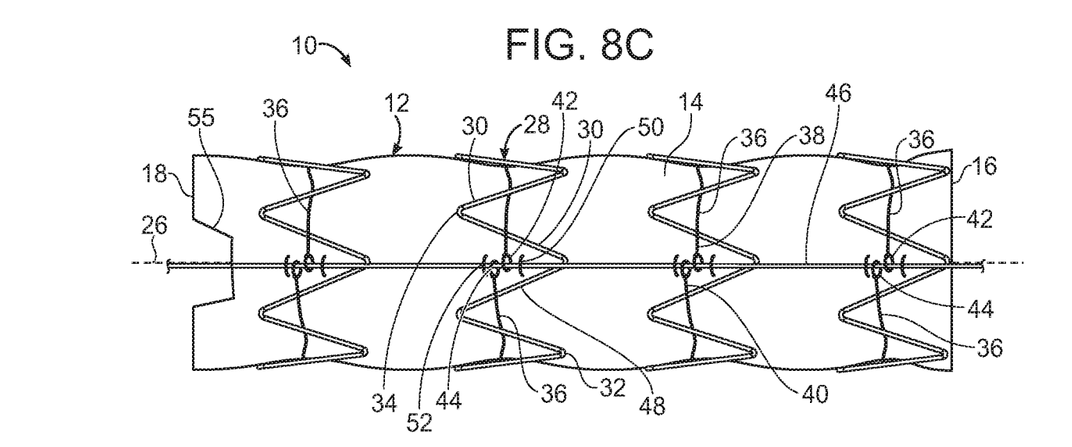
FIG. 8C is a side view of a further embodiment of a stent graft delivery system of the invention, wherein the distal open end includes a scalloped edge.
Figure 8D:
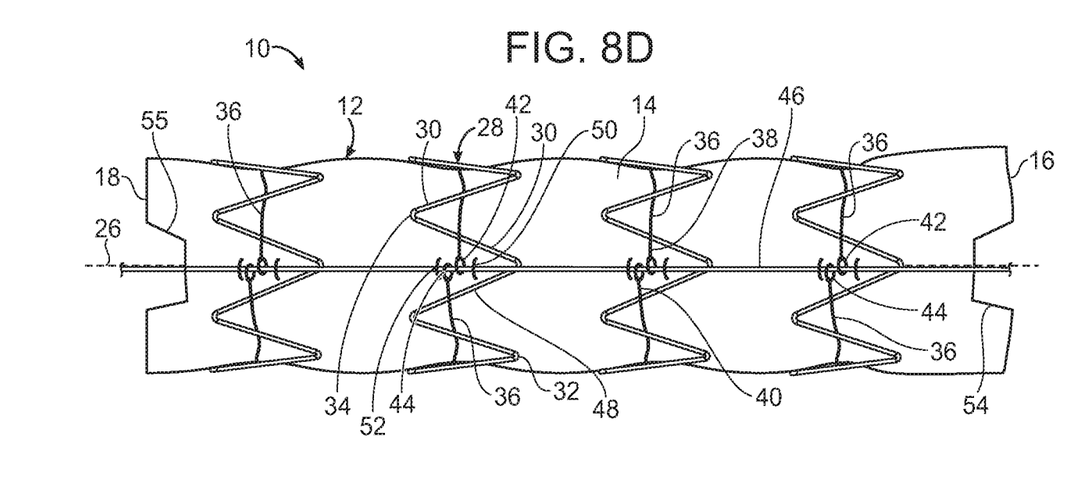
FIG. 8D is a side view of a further embodiment of a stent graft delivery system of the invention, wherein both the proximal and distal open ends include a scalloped edge.

As shown in FIGS. 8A through 8D, stent graft 10 can include at least one proximal fenestration 53 (FIG. 8A), a scalloped proximal open end 54 (FIG. 8B), a scalloped distal open end 55 (FIG. 8C) and a scalloped proximal and distal open ends 54,55, respectively (FIG. 8D). Although not shown, stent graft 10 can include at least one fenestration in combination with at least one of a scalloped proximal open end and a scalloped distal open end. In additional embodiments, the stent grafts of the invention can include a bare stent at at least one of the proximal open end and distal open end that, optionally, include barbs at respective proximal or distal apices (not shown).

Figures 9, 10A, 10B:
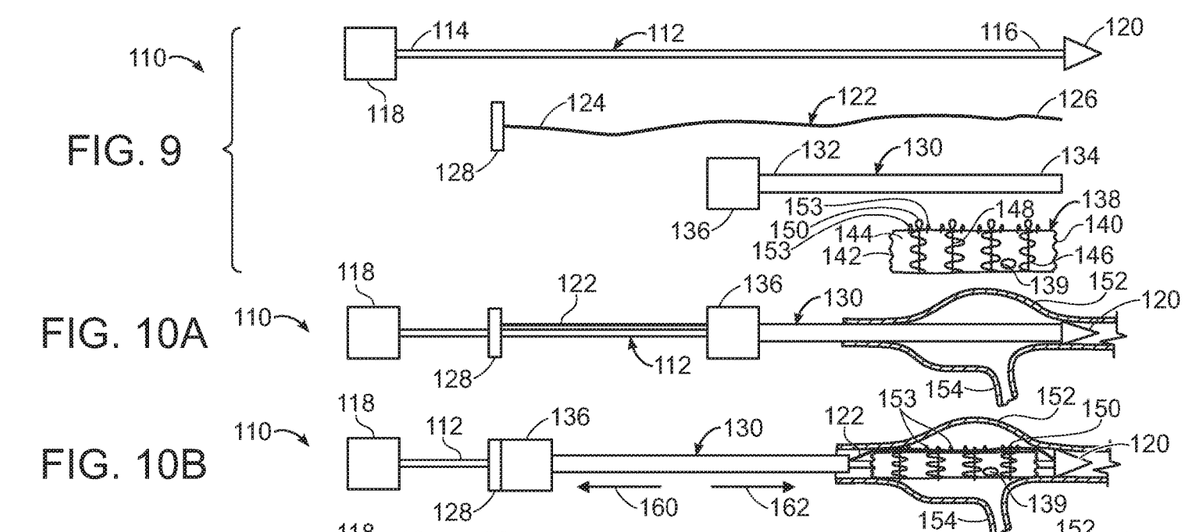
FIG. 9 is an exploded side view of one embodiment of a stent graft delivery system of the invention.
FIG. 10A is a side view of the stent graft delivery system shown in FIG. 9, but in assembled form and, wherein the introducer sheath, containing a stent graft of the stent graft delivery system of the invention, has been delivered to an arterial aneurysm of a patient.
FIG. 10B is a side view of the stent graft delivery system of FIG. 10A, following proximal retraction of the introducer sheath along the stent graft delivery device, to thereby expose the stent graft, which is held in a radially constricted position by a wire of the stent graft delivery system.

FIG. 9 is an exploded side view of another embodiment of the stent graft delivery system of the invention. As shown therein, stent graft delivery system 110 includes guidewire catheter 112 having proximal end 114 and distal end 116. Proximal handle 118 is fixed to proximal end 114 of guidewire catheter 112. Nose cone 120 is fixed to distal end 116 of guidewire catheter 112. Wire 122 includes proximal end 124 and distal end 126. Wire 122 can be fabricated of a suitable material, such as is known in the art, including, for example, Nitinol or some other shape memory alloy. Wire 122 is sufficiently flexible not to injure the patient during advancement to an aortic aneurysm of a patient. Wire handle 128 is fixed at proximal end 124 of wire 122. Introducer sheath 130 includes proximal end 132 and distal end 134, and distal handle 136 is fixed to proximal end 132 of introducer sheath 130. Stent graft 138 includes proximal end 140, distal end 142, luminal graft component 144, stents 146 distributed along luminal graft component 144, and ligatures 148, arranged and configured as discussed above.

FIG. 10A is an assembled side view of stent graft delivery system 110 shown in FIG. 9, wherein stent graft 138 has been loaded within distal end 134 of introducer sheath 130, and radially constricted, at least in part, by wire 122 threaded through loops 150 at ends of ligatures 148, as discussed above, and through stabilizing anchor loops 153. In an embodiment, stent graft 138 includes fenestration 139. In a method of the invention, stent graft delivery system 110 is advanced to arterial aneurysm 152 of a patient. In one embodiment, shown in FIG. 10A, introducer sheath 130 is advanced to aneurysm site 152 to thereby place stent graft 138 at arterial aneurysm 152. As can be seen in FIG. 10B, distal handle 136 is retracted in a proximal direction indicated by arrow 160 toward proximal handle 118, thereby retracting introducer sheath 130 from stent graft 138 at aneurysm 152. As can be seen in FIG. 10B, despite retraction of introducer sheath 130, stent graft 138 is maintained in a radially constricted position by wire 122 extending through ligature loops 150 of ligatures 148 traversing struts of stents 146 distributed longitudinally along stent graft 138. It is to be understood, however, that in alternative embodiments, stent graft delivery system 110 can be advanced within an artery to a position distal to arterial aneurysm 152, wherein stent graft 138 is directed to arterial aneurysm 152 by advancement of proximal handle 118 and wire handle 128 in a distal direction indicated by arrow 162 toward distal handle 136 to thereby direct radially constricted stent graft 118 from introducer sheath 130 to arterial aneurysm 152.

Figures 10C, 10D:
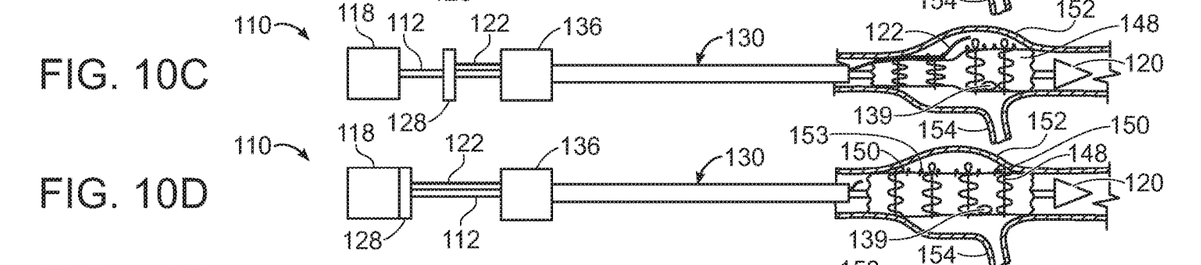
FIG. 10C is a side view of the stent graft delivery system shown in FIGS. 10A and 10B, following partial retraction of the wire from ligatures that, when linked by the wire, holds the stent graft in a partially radially constricted position, while the remainder of the stent graft is in a radially expanded position.
FIG. 10D is a side view of the graft prosthesis delivery system shown in FIGS. 10A-10C, following full retraction of the wire from the stent graft, whereby the stent graft is in a radially expanded position along its entire length.
Figure 10E:
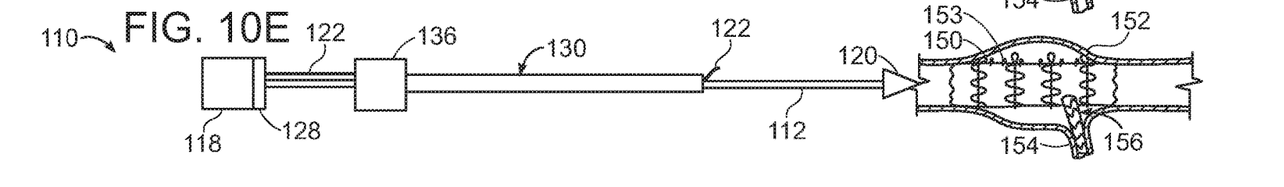
FIG. 10E is a side view of the stent graft delivery system shown in FIGS. 10A through 10D, following retraction of the remainder of the stent graft delivery system not implanted at the aneurysm, whereby implantation of the stent graft at the aneurysm of the patient is complete.

Following direction of stent graft to a position that spans aneurysm 152, and at least partial rotational and axial alignment of stent graft at aneurysm 152, wire 122 is partially retracted from loops 150 of ligatures and from anchor loops 153. Proximal retraction of wire handle 128 toward proximal handle 118, in the direction indicated by arrow 160, as can be seen in FIG. 10C. Continued retraction of wire 122 withdraws wire 122 from all of suture loops 150 of ligatures 148 and anchor loops 153, thereby enabling stent graft 138 to fully expand from its radially constricted state, shown in FIG. 10B, to a radially expanded state, shown in FIG. 10D. In an embodiment, stent graft 138 is positioned so that fenestration 139 is properly aligned with arterial branch 154 for subsequent placement of branch prosthesis 156 through fenestration 139 to arterial branch 154. Thereafter, stent graft 138 is fully implanted within aneurysm, and the remainder of stent graft delivery device 110 is retracted from stent graft 138 and the patient, as shown in FIG. 10E, thereby completing treatment of aneurysm site 152 of the patient by the method of the invention.

Vascular prostheses implanted by the stent graft systems and methods of the invention can be implanted, for example, by transfemoral access. Additional branch prostheses that are directed into the vascular prostheses of the invention can be implanted, for example, by supraaortic vessel access (e.g., through the brachial artery), or by transfemoral access, or access from some other branch or branches of major blood vessels, including peripheral blood vessels.

The teachings of all patents, published applications and references cited herein are incorporated by reference in their entirety. The relevant teachings of all patents, published applications and references cited herein are incorporated by reference in their entirety. The relevant teachings of U.S. Pat. Nos. 8,292,943; 7,763,063; 8,308,790; 8,070,790; 8,740,963; 8,007,605; 9,320,631; 8,062,349; 9,198,786; 8,062,345; 9,561,124; 9,173,755; 8,449,595; 8,636,788; 9,333,104; 9,408,734; 9,408,735; 8,500,792; 9,220,617; 9,364,314; 9,101,506; 8,998,970; 9,554,929; 9,439,751; 9,592,112; 9,655,712; 9,827,123; 9,877,857; 9,907,686; U.S. patent application Ser. Nos. 14/575,673; 15/166,818; 15/167,055; 14/272,818; 14/861,479; 15/478,424; 15/478,737; 15/587,664; 15/604,032; 15/672,404; 15/816,772; 15/839,272; 15/417,467; PCT/US2017/025844; PCT/US2017/025849; PCT/US2017/025912; PCT/US2017/034223 and PCT/US2017/046062, are also incorporated by reference in their entirety.

The relevant teachings of International Application Numbers: PCT/US2018/019355; PCT/US2018/019344; PCT/US2018/019349; PCT/US2018/019353; PCT/US2018/019354; PCT/US2018/019352; PCT/US2018/019350; PCT/US2018/019356; PCT/US2018/019351; PCT/US2018/019510, are also incorporated by reference in their entirety.

While example embodiments have been particularly shown and described, it will be understood by those skilled in the art that various changes in form and details may be made therein without departing from the scope of the embodiments encompassed by the appended claims.

What is claimed is:

1. A stent graft, comprising:
   a) a luminal graft component having a proximal open end and a distal open end;
   b) a plurality of stents distributed longitudinally along the luminal graft component, at least one of the stents having struts that are joined to define proximal and distal apices;
   c) at least one ligature, each ligature traversing at least a portion of the struts of at least one of the stents, the ligature including ends that, when linked, at least partially radially constrict each corresponding stent; and
   d) a pair of anchor loops at the luminal graft component that are distributed longitudinally along the luminal graft component and thereby longitudinally span the ends of each associated ligature when the ends of each associated ligature are linked by a wire, thereby causing each associated ligature to radially constrict each corresponding stent, the pair of anchor loops thereby stabilizing the wire and preventing lateral migration of the wire during implantation of the stent graft.

2. The stent graft of claim 1, wherein the ligature extends completely about a circumference of the stent when the ends are linked.

3. The stent graft of claim 1, wherein at least a portion of the ligatures are each circular and can be linked at diametrically opposed points by a wire threading the anchor loops when the ligature is radially constricting the luminal graft component.

4. The stent graft of claim 1, further including ligature sutures arranged laterally at the luminal graft component through which the ligature ends pass, the ligature sutures being located on either lateral side of a wire passing through the anchor loops, and wherein the ligature ends are linked by the wire between the ligature sutures.

5. The stent graft of claim 1, wherein the ligature is a thread.

6. The stent graft of claim 5, wherein the thread includes at least one member of the group consisting of polyester, nylon, expanded polytetrafluoroethylene (ePTFE), polyvinylidene fluoride (PVDF), and polypropylene.

7. The stent graft of claim 1, wherein at least a portion of the stents includes a shape-memory alloy.

8. The stent graft delivery system of claim 7, wherein the shape-memory alloy includes Nitinol.

9. The stent graft of claim 8, wherein at least a portion of the stents include a radiopaque material.

* * * * *